United States Patent [19]
Ota

[11] Patent Number: 5,248,299
[45] Date of Patent: Sep. 28, 1993

[54] SYRINGE APPARATUS INCLUDING READILY REMOVABLE SYRINGE SUPPORTING HEAD

[76] Inventor: Tetsuo Ota, 1126 Almon Cir., Gillette, Wyo. 82716

[21] Appl. No.: 808,212

[22] Filed: Dec. 16, 1991

[51] Int. Cl.⁵ .............................................. A61M 5/00
[52] U.S. Cl. ...................................... 604/110; 604/111; 604/195; 604/218; 604/240; 128/919
[58] Field of Search ............... 604/110, 111, 192, 187, 604/194–198, 218, 240, 263; 128/919, 763; 206/364–366

[56] References Cited

U.S. PATENT DOCUMENTS

| | | | |
|---|---|---|---|
| 2,578,394 | 12/1951 | Blackman | 604/194 |
| 3,320,954 | 5/1967 | Cowley | 604/110 |
| 4,027,669 | 6/1977 | Johnston et al. | 604/110 |
| 4,220,151 | 9/1980 | Whitney | 604/110 |
| 4,966,593 | 10/1990 | Lennox | 604/198 |
| 5,000,738 | 3/1991 | LaVollo et al. | 604/110 |
| 5,098,404 | 3/1992 | Collins | 604/199 |
| 5,129,888 | 7/1992 | Bidoia | 604/240 |

FOREIGN PATENT DOCUMENTS

| | | | |
|---|---|---|---|
| 2613230 | 10/1988 | France | 604/110 |
| 0573611 | 11/1945 | United Kingdom | 604/195 |
| 2210270 | 6/1989 | United Kingdom | 604/110 |

Primary Examiner—John D. Yasko
Assistant Examiner—Mark O. Polutta
Attorney, Agent, or Firm—Leon Gilden

[57] ABSTRACT

A syringe is arranged with a frangible connection between a conical needle head mounting a needle member to permit removal of the head and associated needle member permitting projection of the needle into the syringe body subsequent to its use. A modification of the invention includes a container to receive used needle bodies, with indicator dye contained within the capsule within the needle body that is ruptured upon insertion of the needle therewithin for indication of a used needle within a storage container.

2 Claims, 4 Drawing Sheets

SYRINGE APPARATUS INCLUDING READILY REMOVABLE SYRINGE SUPPORTING HEAD

BACKGROUND OF THE INVENTION

1. Field of the Invention

The field of invention relates to syringe apparatus, and more particularly pertains to a new and improved syringe apparatus wherein the same is arranged for sanitary disposal of a syringe member subsequent to use.

2. Description of the Prior Art

Syringe apparatus of various types are utilized throughout the prior art and typically in contemporary society, the advent of various virus and disease mandates a secure manner of disposal of a syringe subsequent to its use. Such apparatus is exemplified in the U.S. Pat. No. 4,961,728 to Kosinki; U.S. Pat. No. 4,966,593 to Lennox; U.S. Pat. No. 4,955,869 to Bin; U.S. Pat. No. 4,950,240 to Greenwood, et al.

Accordingly, it may be appreciated that the prior art has not provided for the disposal of a needle member relative to the body in a manner as set forth by the instant invention and in this respect, the present invention substantially fulfills this need.

SUMMARY OF THE INVENTION

In view of the foregoing disadvantages inherent in the known types of syringe apparatus now present in the prior art, the present invention provides a syringe apparatus wherein the same is arranged for the reception of the needle within the syringe body subsequent to use. As such, the general purpose of the present invention, which will be described subsequently in greater detail, is to provide a new and improved syringe apparatus which has all the advantages of the prior art syringe apparatus and none of the disadvantages.

To attain this, the present invention provides a syringe arranged with a frangible connection between a conical needle head mounting a needle member to permit removal of the head and associated needle member with the possibility of permitting projection of the needle into the syringe body subsequent to its use. A modification of the invention includes a container to receive used needle bodies, with indicator dye contained within the capsule within the needle body that is ruptured upon insertion of the needle therewithin for indication of a used needle within a storage container.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the purposes of the present invention. It is important, therefore, that the claims be regarded as including such equivalent constructions insofar as they do not depart from the spirit and scope of the present invention.

It is therefore an object of the present invention to provide a new and improved syringe apparatus which has all the advantages of the prior art syringe apparatus and none of the disadvantages.

It is another object of the present invention to provide a new and improved syringe apparatus which may be easily and efficiently manufactured and marketed.

It is a further object of the present invention is to provide a new and improved syringe apparatus which is of a durable and reliable construction.

An even further object of the present invention is to provide a new and improved syringe apparatus which is susceptible of a low cost of manufacture with regard to both materials and labor, and which accordingly is then susceptible of low prices of sale to the consuming public, thereby making such syringe apparatus economically available to the buying public.

Still yet another object of the present invention is to provide a new and improved syringe apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
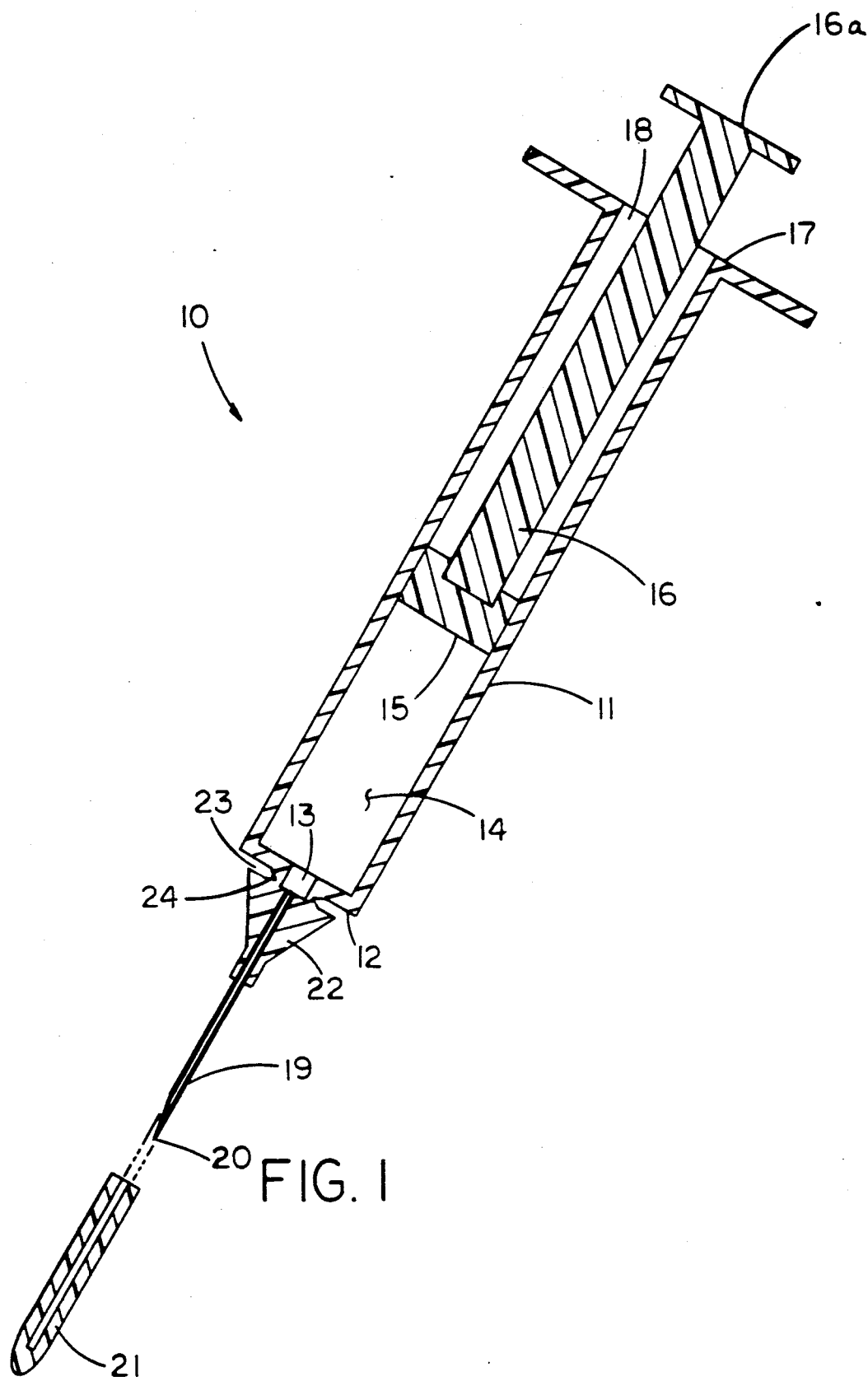
FIG. 1 is an orthographic side view in cross-section of the instant invention.

With reference now to the drawings, and in particular to FIGS. 1 to 7 thereof, a new and improved syringe apparatus embodying the principles and concepts of the present invention and generally designated by the reference numerals 10 and 10a will be described.

Figure 2:
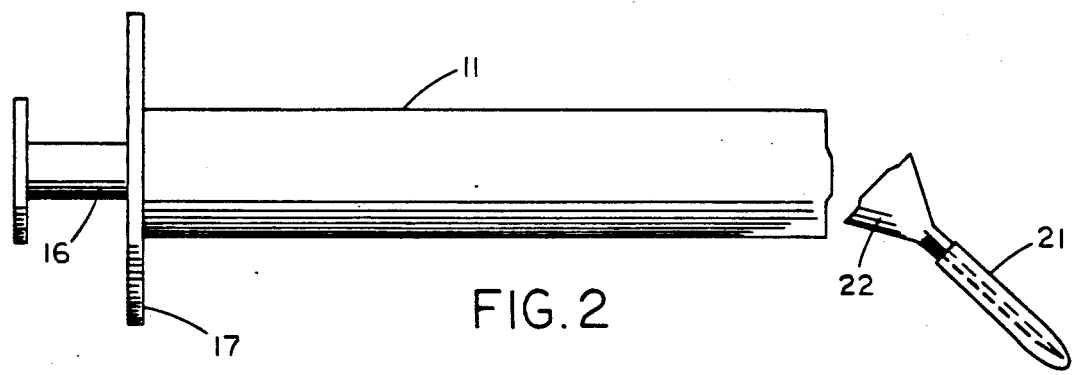
FIG. 2 is an orthographic side view of the invention subsequent to use in a medial disposal step.
Figure 3:
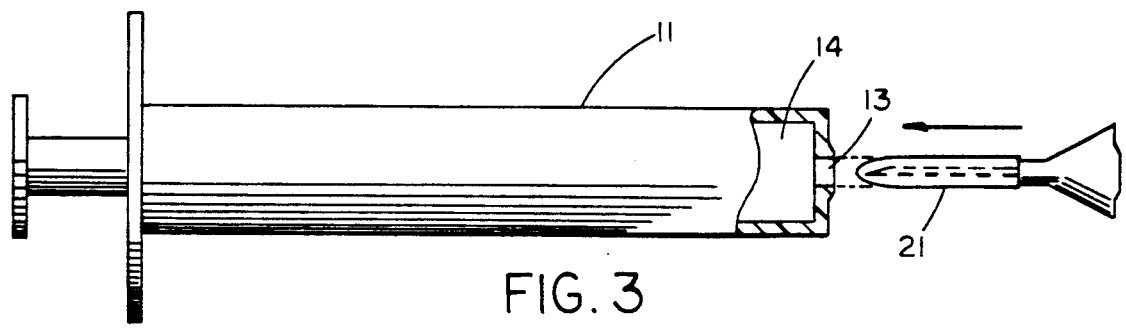
FIG. 3 is an orthographic side view, partially in section, of the invention in a further disposal step.
Figure 4:
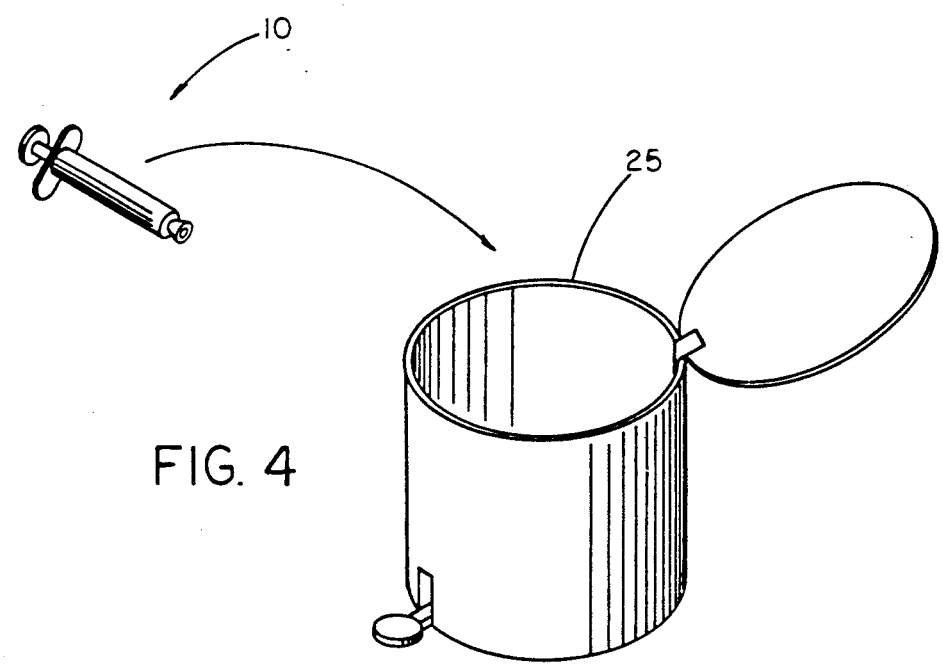
FIG. 4 is an isometric illustration of the invention disposed within an appropriate receptacle.

More specifically, the syringe apparatus 10 of the instant invention essentially comprises an elongate coaxially aligned cylindrical body 11, including a body bottom wall 12 at a lowermost end thereof spaced from a body entrance opening 18 at an upper distal end thereof. A body flange 17 is arranged in surrounding adjacency relative to the entrance opening 18 orthogonally oriented thereto. The bottom wall 12 includes a bottom wall fluid port 13 in communication with a fluid cavity 14 between the bottom wall and an associated syringe piston 15 slidably mounted within the cylindrical body 11. The syringe piston 15 is orthogonally mounted to a piston plunger rod 16 coaxially and fixedly mounted to a syringe piston 15, with the plunger rod 16 extending coaxially through the entrance opening 18 terminating in a head portion 16a. A needle cannula 19 is coaxially and fixedly mounted to a conical needle head 22. The needle 19 receives a cover sheath 21 thereover prior to its use. The needle 19 terminates in a sharpened forward end 20. The conical needle head 22 is fixedly secured in a coaxially aligned relationship relative to the bottom wall 12 about a frangible cylindrical connecting web 24 that is arranged in surrounding relationship relative to the fluid port 13. A circular groove 23 is thereby defined between the floor 12 and the needle head 22. The connecting web 24 is thereafter readily separated from the bottom wall, in a manner as illustrated in FIG. 2, subsequent to use of the syringe apparatus and thereafter the needle cannula 19, or if desired the cannula and the associated sheath 21 are inserted into the fluid port 13 projected into the cavity 14 for disposal into an appropriate dispensing container 25.

Figure 5:
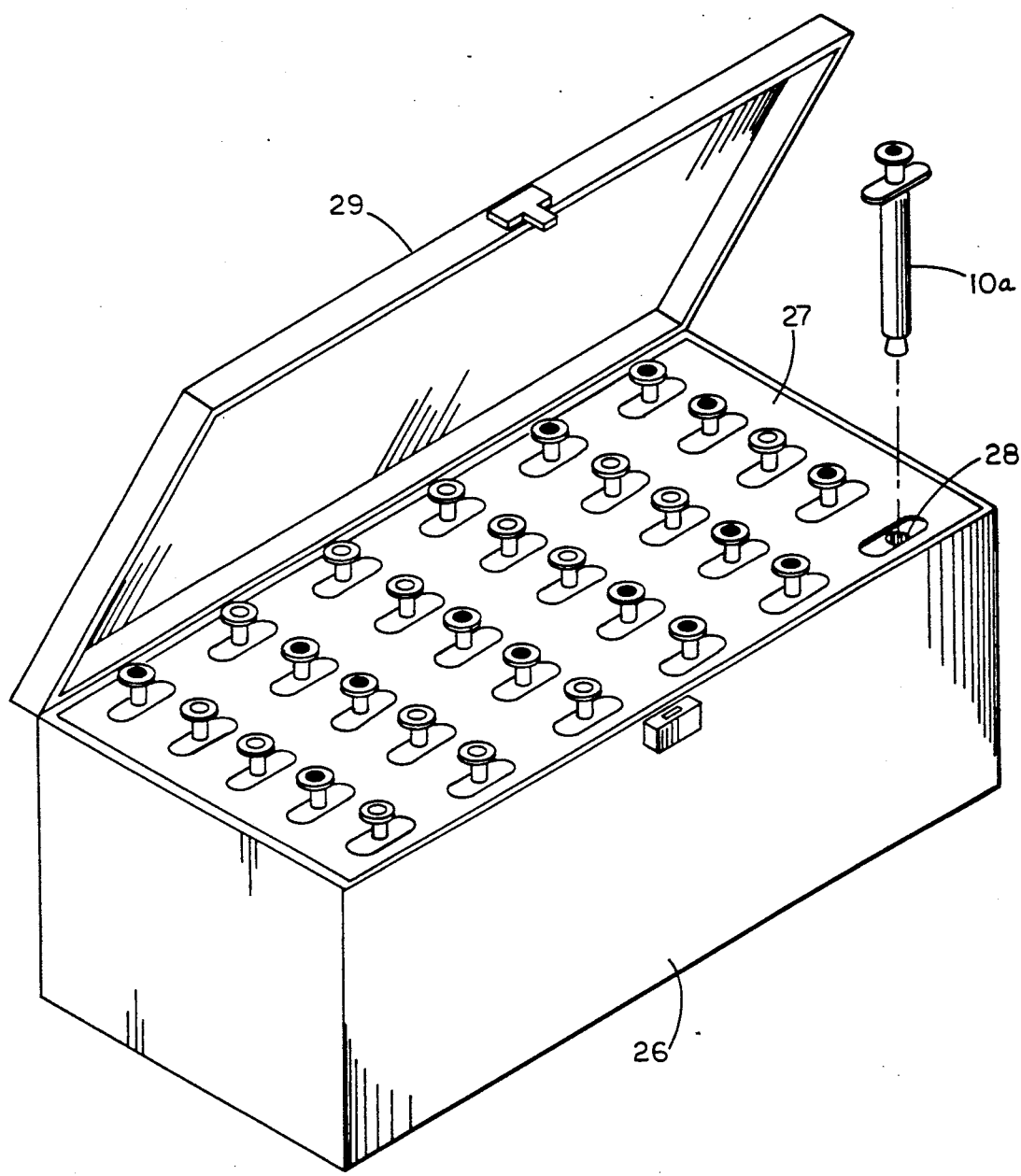
FIG. 5 is an isometric illustration of a modification of the invention utilizing a dispensing housing for receiving disposed syringe members, as well as the storage of unused syringe members.
Figure 6:
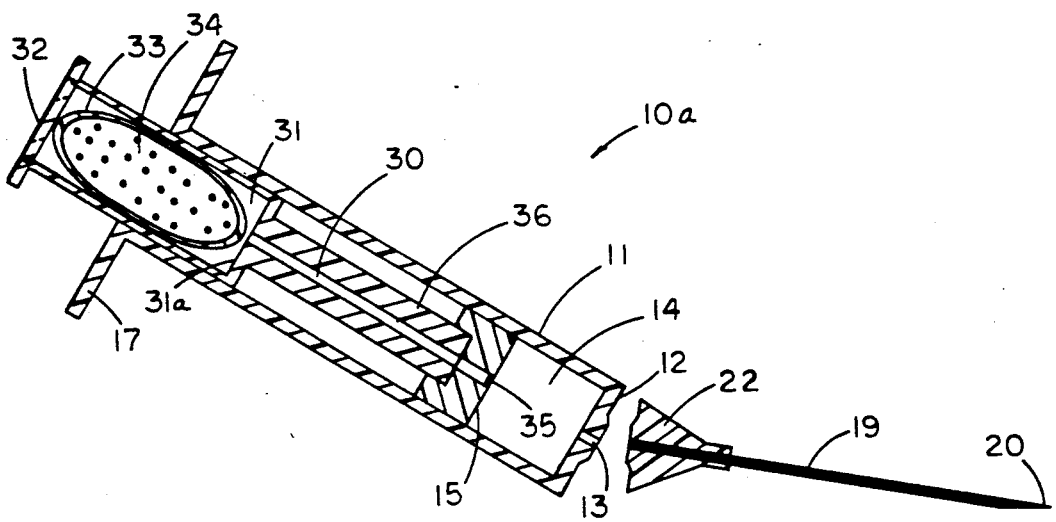
FIG. 6 is an orthographic side view of the modification of the invention.

An alternative apparatus 10a is illustrated in the FIG. 5 for use in association with a dispensing container 25 that includes a housing 26, with a lid 29 hingedly mounted thereto. The housing 26 includes an upper floor plate 27 positioned adjacent an upper distal end of the housing 26, including a matrix of floor openings 28 therethrough receiving the syringe apparatus, and more specifically, the bodies 11 therethrough. The modified syringe 10a, as illustrated in the FIGS. 5-7, includes a piston 15 formed with a plunger rod coaxial bore 30 coaxially directed through the modified plunger rod lower body 36. The lower body 36 is spaced from a plunger rod transparent top wall 32 that is orthogonally oriented relative to the bore 30 defining a plunger rod cavity 31 between the plunger rod top wall 32 and a plunger rod cavity floor 31a that in turn defines an upper distal end of the plunger rod lower body 36. A capsule 33, including a dye solution 34, is positioned within the plunger rod cavity 31, whereupon in termination of use of the syringe, the needle 19 is projected into the fluid port 13 through the plunger rod coaxial bore 30 to pierce the dye solution 34. The transparent top wall 32 thereafter permits visual inspection within the container 25 to indicate which syringe members have been utilized by the darkened appearance through the transparent top wall 32. It should be noted therefore that initially the capsule 33 is of an opaque construction and in release of the dye solution, the dye becomes visually apparent through the top wall 32 in a manner as noted above.

Figure 7:
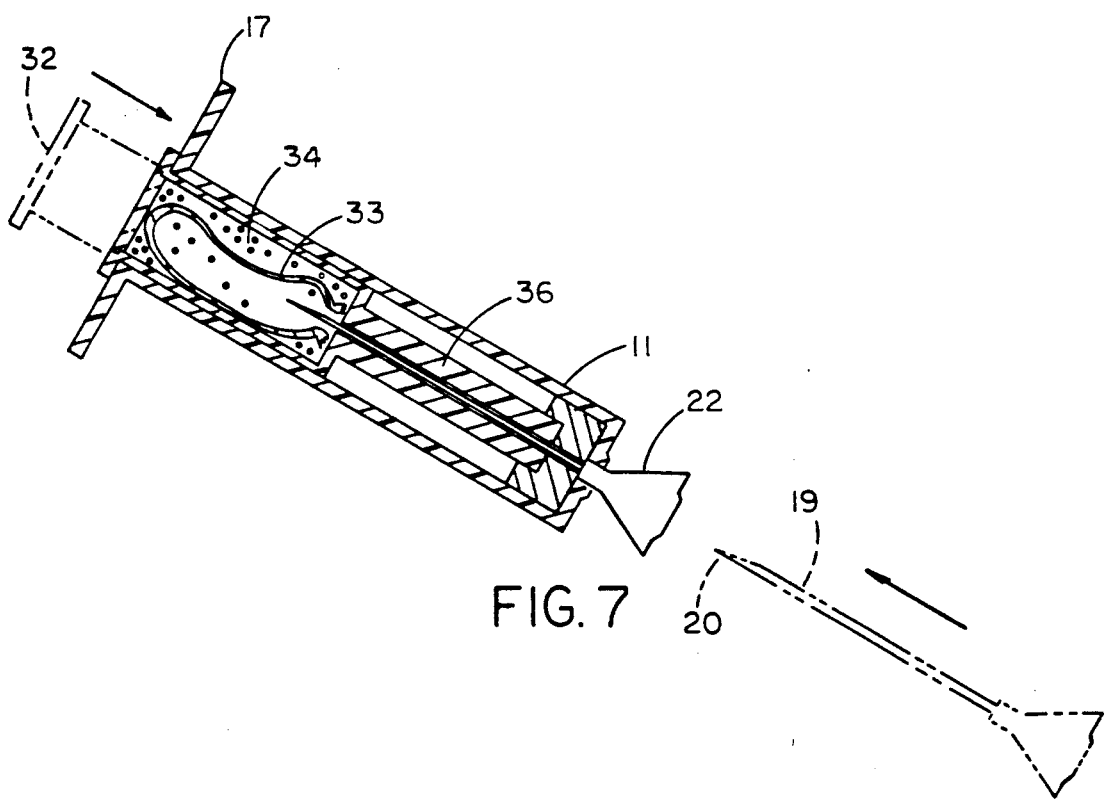
FIG. 7 is an orthographic side view of the modification of the invention in a disposed configuration.

The coaxial bore 30 includes an entrance opening that is in planar alignment with the piston 15 that in turn is in confronting relationship relative to the bottom wall 12, as the entrance opening to the coaxial bore includes a membrane 35 that effects a fluid sealing relative to the cavity 14 during use of the syringe but is subsequently pierced by the needle 19 when projecting the needle through the coaxial bore, in a manner as illustrated in the FIG. 7.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A syringe apparatus, the syringe apparatus including a cylindrical body, the cylindrical body including a bottom wall, and
   a fluid port coaxially directed through the bottom wall, and
   the cylindrical body including a body entrance opening at an upper distal end of the body spaced from the bottom wall, and
   a syringe piston slidably mounted within the cylindrical body, with a fluid cavity oriented between the syringe piston and the bottom wall, and
   the syringe piston including a piston plunger rod mounted coaxially and integrally to the piston projecting rearwardly of the piston extending through the entrance opening, with the plunger rod terminating in a head portion exteriorly of the cylindrical body, and
   a needle head mounted to the bottom wall, with the needle head including a needle member mounted coaxially to the needle head projecting coaxially of and exteriorly of the cylindrical body, with the needle in coaxial alignment with the fluid port, and
   a circular groove defined between a bottom surface of the needle head and an exterior surface of the bottom wall, and
   a cylindrical frangible connecting web extending from the bottom wall to the needle head coaxially aligned relative to the needle head and the cylindrical body, wherein the needle head is arranged for removal from the bottom wall by displacement of the needle head relative to the bottom wall permitting subsequent reception of the needle within the cavity through the fluid port, and
   the plunger rod includes a coaxial bore directed therethrough, and the head portion of the plunger rod is transparent and spaced from a plunger rod cavity floor, wherein a plunger rod cavity is oriented between the plunger rod cavity floor and the transparent head portion, and wherein the plunger rod cavity floor is oriented parallel relative to a forward face of the piston in confronting relationship relative to the cylindrical body bottom wall within the cavity, and an opaque capsule containing a dye solution positioned within the plunger rod cavity between the transparent head portion and the plunger rod cavity floor, and the needle is receivable within the plunger rod cavity through the coaxial bore.

2. An apparatus as set forth in claim 1 wherein the coaxial bore terminates in an entrance opening through the forward face of the piston and wherein the entrance opening includes a membrane coplanar with the forward face of the piston arranged for rupture upon projection of the needle member therethrough, wherein the needle member is arranged for projection into the plunger rod cavity for rupture of the capsule for visual observation of the dye solution through the transparent head portion.

* * * * *